US008748336B2

(12) United States Patent
Arrowood et al.

(10) Patent No.: US 8,748,336 B2
(45) Date of Patent: *Jun. 10, 2014

(54) ALKOXYLATION PROCESSES AND CATALYSTS THEREFOR

(75) Inventors: Tina L. Arrowood, Coleman, MI (US); Paul R. Elowe, Midland, MI (US); Jason C. MacDonald, Bay City, MI (US); Ernesto Occhiello, Horgen (CH)

(73) Assignee: Dow Global Technologies LLC, Midland, MI (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/142,296

(22) PCT Filed: Feb. 25, 2010

(86) PCT No.: PCT/US2010/025394
§ 371 (c)(1),
(2), (4) Date: Jun. 27, 2011

(87) PCT Pub. No.: WO2010/099307
PCT Pub. Date: Sep. 2, 2010

(65) Prior Publication Data
US 2011/0301323 A1 Dec. 8, 2011

Related U.S. Application Data
(60) Provisional application No. 61/155,786, filed on Feb. 26, 2009.

(51) Int. Cl.
B01J 23/32 (2006.01)
B01J 27/24 (2006.01)
B01J 23/00 (2006.01)
B01J 27/00 (2006.01)
C08G 59/68 (2006.01)

(52) U.S. Cl.
USPC ........... 502/306; 502/200; 502/305; 502/311; 502/313; 528/409; 528/410; 528/412

(58) Field of Classification Search
USPC .......... 502/200, 305, 306, 311, 313; 528/409, 528/410, 412
See application file for complete search history.

(56) References Cited

U.S. PATENT DOCUMENTS

| 5,342,903 | A | 8/1994 | Wolleb et al. |
| 6,376,721 | B1 | 4/2002 | Priou et al. |
| 6,448,414 | B1 | 9/2002 | Jacobsen et al. |
| 6,492,565 | B2 | 12/2002 | Denninger et al. |
| 6,624,321 | B2 | 9/2003 | Denninger et al. |
| 6,693,206 | B2 | 2/2004 | Liu et al. |
| 6,800,766 | B2 | 10/2004 | Jacobsen et al. |
| 6,846,961 | B2 | 1/2005 | Teles |
| 6,998,497 | B2 | 2/2006 | Earle et al. |
| 7,220,870 | B2 | 5/2007 | Jacobsen et al. |

FOREIGN PATENT DOCUMENTS

| CN | 101270113 A | 9/2008 |
| DE | 195 25 067 A1 | 1/1997 |
| DE | 10 2008 002091 A1 | 12/2008 |
| EP | 1380342 A1 | 1/2004 |
| JP | 2005305280 A | 11/2005 |
| KR | 2008019391 A | 3/2008 |
| WO | WO-01/00552 A1 | 1/2001 |
| WO | WO-2009/014362 A2 | 1/2009 |
| WO | WO-2009/026261 A2 | 2/2009 |

OTHER PUBLICATIONS

U.S. Appl. No. 13/142,297 claims.*
Azoulay, Stephane, Kei Manabe, et al. "Catalytic Asymmetric Ring Opening of meso-Epoxides wih Aromatic Amines in Water." Organic Letters. 7.21 (2005): 4593-95.
Brown, Lynda J., Ian B. Spurr, et al. "Total Synthesis of cis-Sylvaticin." Orangic Letters. 10.12 (2008): 2489-92.
Ding, Rui, Kambiz Katebzadeh, et al. "Expanding the Scope of Lewis Acid Catalysis in Water: Remarkable Ligand Acceleration of Aqueous Ytterbium Triflate Catalyzed Michael Addition Reations." Journal of Organic Chemistry. 71.1 (2006): 352-5.
Dioos, Bart M.L., and Pierre A. Jacobs. "Heterogenisation of dimeric Cr(salen) with supported ionic liquids." Journal of Catalysis. 243. (2006): 217-19.
Fukuzawa, Shin-Ichi, Yuusuke Yahara, et al. "Stereoselective Pinacol Coupling of Chiral Formylferrocene Using Divalent Samarium Triflate: Preparation of a New Chiral Disferrocenyl Oxazoline Ligand and Its Application to Asymmetric Diels-Alder Reactions." Organic Letters. 7.26 (2005): 5809-12).
Jain, Surbhi, Xiaolai Zheng, et al. "Importance of Counterion Reactivity on the Deactivation of Co-Salen Catalysts in the Hydrolytic Kinetic Resolution of Epichlorohydrin." Inorganic Chemistry. 46.21 (2007): 8887-96.
Ji, Chang, Shannon E. Day, and William Silvers. "Catalytic Reduciton of 1-and 2-Bromoocctanes by a Dinickel(I) Schiff Base Complex Containing Two Salen Unites Electrogenerated at Carbon Cathodes in Dimethylformamide." Journal of Electroanalytical Chemistry. 622. (2008): 15-21.
Jia, Yi-Xia, Shuo-Fei Zhu, et al. "Asymmetric Friedel-Crafts Alkylations of Indoles with Nitroalkenes Catalyzed by Zn(II)-Bisoxazoline Complexes." Journal of Organic Chemistry. 71.1 (2006): 75-80.
Kim , Geon-Joong, Hosung Lee, and Seong-Jin Kim. "Catalytic Activity and Recyclability of new Enantioselective Chiral Co-Salen Complexes in the hydrolytic Kinetic Resolution of Epichlorohydrine." Tetrahedron Letters. 44. (2003): 5005-8.
Kim, Geon-Joong, and Dae-Woon Park. "The Catalytic Activity of New Chiral Salen Complexes Immobilized on MCM-41 in teh Asymmetric Hydrolysis of epoxides to Diols." Catalysis Today. 63. (2000): 537-47.
Kobayashi, Shu, Tsuyoshi Ogino, et al. "Bismuth Triflate-Chrial Bipyridine Complexes as Water-Compatible Chiral Lewis Acids." Organic Letters. 7.21 (2005): 4729-31.

(Continued)

Primary Examiner — Duc Truong

(57) ABSTRACT

A process of contacting an alkylene oxide with 2-methoxy-1-propanol (PM1) in the presence of an oligomeric Schiff base metal complex catalyst is disclosed. Further, a process involving contacting an alkylene oxide with an alkyl alcohol using an oligomeric Schiff base metal complex as a catalyst is also disclosed. Additionally, novel compositions which can be used as catalysts in processes involving the contacting of an alkyl alcohol with an alkylene oxide are also disclosed.

8 Claims, No Drawings

(56) References Cited

OTHER PUBLICATIONS

Konsler, Reed G., Jorn Karl, and Eric N. Jacobsen. "Cooperative Asymmetric Catalysis with Dimeric Salen Complexes." *Journal of the American Chermical Society.* 120. (1998): 10780-81.

Kwon, Mi-Ae, and Geon-Joong Kim. "Synthesis of Polymeric Salen Complexes and Application in the Enantioselective Hydrolytic Kinetic Resolution of Epoxides as Catalysts." *Catalysis Today.* 87. (2003): 145-51.

Martinez, Luis E., James L. Leighton, Douglas H. Carsten, and Eric N. Jacobsen. "Highly Enantioselective Ring Opening of Epoxides Catalyzed by (salen)Cr(III) Complexes." *Journal of the American Chemical Society.* 117. (1995): 5897-98.

Mazet, Clement, and Eric N. Jacobsen. "Dinuclear {(salen)Al} Complexes Display Expanded Scope in the Conjugate Cyanation of $\alpha,\beta$-Unsaturated Imides." *Angewandte Chemie International Edition.* 47. (2008): 1762-65.

Nakamura, Yuki, et al, and Hisashi Okawa. "Tetranuclear Mixed-Metal $M^{II}_2CU^{II}_2$ Complexes Dervied from a Phenol-Based Macrocyclic Ligand Having Two $N(amine)_2O_2$ and Two $N(imine)_2O_2$ Metal-Binding Sites." *Inorganic Chemistry.* 40. (2001): 3739-44.

Ready, Joseph M., and Eric N. Jacobsen. "A Practical Oligomeric [(salen)Co] Catalyst for Asymmetric Epoxide Ring-Opening Reactions." *Angewandte Chemie International Edition.* 41.8 (2002): 1374-77.

Ready, Joseph M., and Eric N. Jacobsen. "Asymmetric Catalytic Synthesis of $\alpha$-Aryloxy Alcohols: Kinetic Resolution of Terminal Epoxides via Highly Enantioselective Ring_opening with Phenols." *Journal of the American Chemical Society.* 121. (1999): 6086-87.

Ready, Joseph M., and Eric N. Jacobsen. "Highly Active Oligomeric (salen) Co Catalysts for Asymmertirc Epoxide Ring-Opening Reactions." *Journal of the American Chemical Society.* 123. (2001): 2687-88.

Schon, Eva, Xiangyang Zhang, et al. "Gas-Phase and Solution-Phase Polymerization of Epoxides by Cr(salen) Complexes: Evidence for a Dinuclear Cationic Mechanism." *Inorganic Chemistry.* 43.23 (2004): 7278-80.

Shimakoshi, Hisashi, Akihiro Goto, et al. "Synthesis and Redox Behavior of Dialkylated Dicobalt Complexes having Two Discrete Salen Units." *Tetrahedron Letters.* 42. (2001): 1949-1951.

Shimakoshi, Hisashi, Hiroki Takemoto, et al. "New Macrocyclic Ligands having Discrete Metal Binding Sites." *Tetrhedron Letters.* 43.27 (2002): 4809-12.

Shimakoshi, Hisashi, Wataru Ninomiya, and Yoshio Hisaeda. "Reductive coupling of benzyl bromide catalyzed by a novel dicobalt complex having two salen units." *Journal of the Chemcial Society, Dalton Transactions.* 13. (2001): 1971-74.

Tokunaga, Makoto, Jay F. Larrow, Fumitoshi Kakiuchi, and Eric N. Jacobsen. "Asymmetric Catalysis with Water: Efficient Kinetic Resolution of Terminal Epoxides by Means of Catalytic Hydrolysis." *Science.* 277. (1997): 936-938.

White, "Development and mechanistic studies of a highly active and selective oligomeric (salen)co(III) catalyst for asymmetric epoxide ring opening reactions" *Harvard University Thesis* (2005),p. 55, p. 169-174.

White, David E. and Eric N. Jacobsen "New Oligomeric Catalyst for the Hydrolytic Kinetic Resolution of Terminal Eposides under Solvent-Free Conditions." *Tetrahedron: Asymmetry.* 14. (2003): 3633-38.

Wu, Michael H., Karl B. Hansen, and Eric N. Jacobsen. "Regio- and Enantioselective Cyclization of Epoxy Alcohols Catalyzed by a $[Co^{III}(salen0]$ Complex." *Angewandte Chemie International Edition.* 38.13/14 (1999): 2012-14.

Zheng, Xiaolai, Christopher W. Jones, and Marcus Weck. "Ring Expanding Olefin Metathesis: A Route to Highly Active Unsymmetrical Macrocyclic Oligomeric Co-Salen Catalysts for the Hydrolytic Kinetic Resolution of Epoxides." *Journal of the American Chemical Society.* 129. (2007): 1105-12.

\* cited by examiner

ALKOXYLATION PROCESSES AND CATALYSTS THEREFOR

FIELD OF THE INVENTION

This invention relates to novel Schiff base compositions. This invention further relates to contacting an alkylene oxide with an alcohol in the presence of a Schiff base catalyst. This invention also relates to the propoxylation of 2-methoxy-1-propanol and 1-methoxy-2-propanol.

BACKGROUND OF THE INVENTION

The conversion of propylene oxide using base-catalyzed conditions to produce a mixture of monopropylene glycol methyl ethers (PM), dipropylene glycol methyl ether (DPM), tripropylene glycol methyl ethers (TPM) and heavier molecular weight polypropylene glycol methyl ethers is the current industry standard technology for commercial PM glycol ethers. The mixture of the mono-, di-, tri- and heavier product categories can be controlled by adjusting the methanol-to-propylene oxide feed mole ratio, recycling products back to the reactor for further propylene oxide addition, and adjusting the reactor temperature among other means.

The monopropylene glycol methyl ether family includes two isomers, 1-methoxy-2-propanol (PM2) and 2-methoxy-1-propanol (PM1). Using industry standard base-catalyzed technology, the PM2/PM1 ratio is ~20/1. Reaction technology giving a selectivity >20/1 is preferable since PM1 is classified as a teratogen and can be present as a component in the commercial PM2 product at <0.5 wt %. In order to achieve this specification, costly distillation is used to separate these similar boiling materials (PM2 bp=118-119° C.; PM1 bp=130° C.).

Catalytically propoxylating PM1 to propoxylated adducts with very little reaction of PM2 can provide a mixture that is easily separated by simple distillation yet retains the highly desired PM2 product. Moreover, a catalyst system that selectively propoxylates methanol to monopropylene glycol methyl ether and at the same time further catalyzes the selective propoxylation of the undesired PM1 product to DPM can result in a highly selective process for producing PM2.

Although the primary hydroxyl group of PM1 is more acidic than the secondary hydroxyl group of PM2, significant propoxylation of both PM1 and PM2 occurs under base-catalyzed (e.g., NaOH or KOH) conditions.

Therefore, a process in which a Schiff base metal complex is used to selectively catalyze PM1 propoxylation to DPM in the presence of PM2 with very little reaction of PM2 would be desirable. Further, a process which yields very little PM1 by performing selective reaction of methanol with propylene oxide over a Schiff base metal complex catalyst followed by further selective reaction of the undesired PM1 product to DPM over the same Schiff base catalyst would also be desirable. Additionally, novel compositions which can be used as catalysts for the regio selective methanolysis of propylene oxide would also be desirable.

SUMMARY OF THE INVENTION

In accordance with another embodiment of the present invention, there is provided a composition comprising, consisting of, or consisting essentially of a racemic or non-racemic mixture of chiral Schiff base monomers wherein a monomer is defined by formula (I) wherein $R_1$, $R_2$, $R_3$, $R_4$, $Y_1$, $Y_2$, $X_1$, $X_2$, $X_3$, $X_4$, $X_5$, $X_6$, $X_7$, and $X_8$ comprise, independently of one another, substituents selected from the group consisting of hydrogen, halogen, alkyl, alkenyl, alkynyl, hydrocarbyl, hydroxyl, alkoxyl, amino, nitro, amide, phosphoryl, phosphonate, phosphine, carbonyl, carboxyl, silyl, ether, thioether, sulfonyl, selenoether, ketone, aldehyde, and ester; or wherein two or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ together form a ring selected from the group consisting of a carbocyclic ring and a heterocyclic ring, said ring having from 4 to 10 atoms in the ring;

wherein $R_5$ group is selected from the group comprising a carbon-carbon bond, a methylene group, an ethylene group, an amine, an oxygen atom, and a sulfur atom;

wherein one or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ are capable of providing a complementary interaction to form a component selected from the group consisting of oligomer, polymer, and copolymer;

wherein $M^{t+}$ is a Group 2-15 metal capable of complexing with a ligand to affect catalysis, wherein t is an integer between 2 and 4;

wherein A is selected from the group consisting of neutral groups, bound anionic groups, unbound anionic groups and combinations thereof, wherein s is the number of A groups associated with the metal and is an integer between 0 and 2; and wherein said composition is a diastereomeric mixture of components selected from the group consisting of oligomers, polymers, co-polymers, and combinations thereof.

In accordance with an embodiment of the invention, a process is provided, the process comprising, consisting of, or consisting essentially of contacting an alkylene oxide with 2-methoxy-1-propanol (PM1) in the presence of a catalyst comprising a tetradentate Schiff-base metal complex in a reaction zone under reaction conditions to produce a reaction product, said reaction product comprising alkoxylated PM1 with less than 10 alkylene oxide equivalents.

In accordance with another embodiment of the invention, there is provided a process comprising, consisting of, or consisting essentially of contacting an alkylene oxide with an alcohol in the presence of a catalyst comprising a tetradentate Schiff base metal complex in a reaction zone under reaction conditions to produce a reaction product comprising a mixture of at least two components selected from the group consisting of mono-alkoxylated alcohol, di-alkoxylated alcohol, tri-alkoxylated alcohol, and heavy molecular weight alkoxylated alcohols containing not more than 10 alkylene oxide equivalents.

DETAILED DESCRIPTION OF THE INVENTION

"Chiral" describes an object that is non-superimposable on its mirror image.

"Achiral" describes an object that is superimposable on its mirror image.

"Stereoisomers" are isomeric molecules that have the same molecular formula and sequence of bonded atoms (constitution), but which differ in the three dimensional orientations of their atoms in space.

"Diastereomers" are stereoisomers not related through a reflection operation. They are not mirror images of each other.

"Tetradentate" is a chelating agent which has four groups capable of attachment to a metal ion.

A "Schiff base" is a functional group resulting from the condensation of aldehydes or ketones with primary amines.

A "Lewis acid" is a molecule that is an electron-pair acceptor.

In accordance with an embodiment of the invention, there is provided a diastereomeric mixture of oligomers, polymers or copolymers of chiral Schiff base monomers, wherein a monomer is defined by formula (I).

$R_1$, $R_2$, $R_3$, $R_4$, $Y_1$, $Y_2$, $X_1$, $X_2$, $X_3$, $X_4$, $X_5$, $X_6$, $X_7$, and $X_8$ comprise, independently of one another, substituents selected from the group consisting of hydrogen, halogen, alkyl, alkenyl, alkynyl, hydrocarbyl, hydroxyl, alkoxyl, nitro, amide, phosphoryl, phosphonate, phosphine, carbonyl, carboxyl, silyl, ether, thioether, sulfonyl, selenoether, ketone, aldehyde, and ester.

In an embodiment, two or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ can together form a ring selected from the group consisting of a carbocyclic ring and a heterocyclic ring, the ring having from 4 to 10 atoms in the ring.

In an embodiment, $R_5$ is selected from the group comprising a carbon-carbon bond, a methylene group, an ethylene group, an amine, an oxygen atom, and a sulfur atom;

In an embodiment, one or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ are capable of providing a complementary interaction to form a component selected from the group consisting of oligomer, polymer, and copolymer;

A complementary interaction can include: carbon-carbon coupling, condensation, etherification, amide formation, esterification, ring opening polymerizations, olefin metathesis, olefin polymerization such as cationic polymerization, anionic polymerization, radical polymerization, group transfer polymerization, heterogeneous Ziegler-Natta polymerization, and homogeneous Ziegler-Natta polymerization.

$M^{t+}$ is a Group 2-15 metal capable of complexing with a ligand to affect catalysis, wherein t is an integer between 2 and 4;

A is selected from the group consisting of neutral groups, bound anionic groups, unbound anionic groups, and combinations thereof, wherein s is the number of A groups associated to the metal and is an integer between 0 and 2.

The composition can be present as an oligomer, a polymer, or a co-polymer.

In an embodiment of the invention, M is cobalt and A is selected from the group consisting of carboxylate, sulfonate, halide, alkoxide, hexafluorophosphate, tetrafluoroborate, hexafluoroantimonate and bis(trialkylsilyl)amide. In an embodiment of the invention, A is 3-nitrobenzenesulfonate and s=1.

In an embodiment of the invention, the composition is present as an oligomer bound to a support wherein the oligomer is 1-20 repeat units of the above defined monomer. Examples of supports that can be used include, but are not limited to, an organic polymer, an ion-exchange resin, an inorganic support, a metal organic framework, and carbon. The catalyst can be incorporated into or onto the support by any suitable method known to those skilled in the art including, but not limited to, covalent bonding, ionic bonding, hydrogen bonding, metal complexing, encapsulating, and intercalating. The following documents provide examples of such supporting techniques and their entire contents are herein disclosed by reference: Baleizo, et. al. *Chemical Reviews* 2006, 106(9), 3987-4043; Orejón, et al., *Industrial and Engineering Chemical Research* 2008, 47(21), 8032-8036; Yang, et al., *Journal of Catalysis* 2007, 248, 204-212; Kim, et. al., *Catalysis Today* 2000, 63, 537-547.

In an embodiment of the invention, the catalyst can be incorporated into polymeric structures by utilizing any of several different methods. The following documents provide examples of such techniques and their entire contents are herein disclosed by reference. Hu, et al., *Journal of Applied Polymer Science* 2006, 101, 2431-2436 Song, et al., *Tetrahedron Letters* 2003, 44, 7081-7085, Kwon, et al., *Catalysis Today* 2003, 87, 145-151, Gill, et al., *Chemistry—A European Journal* 2008, 14, 7306-7313, Zheng, et al., *Chemistry—A European Journal* 2006, 12, 576-583, Zheng, et al., *Advanced Synthesis and Catalysis* 2008, 350, 255-261.

In an embodiment of the invention, more than one of the composition is present and is joined by a polyfunctional A, wherein A is selected from the group consisting of a polycarboxylate, polysulfonate, and a mixture thereof.

In an embodiment of the invention more than one chiral monomeric composition can be linked with one or more chiral monomers to yield greater catalytic activity than the single monomer. One embodiment of the composition is shown in Formula II below wherein the $M^{t+}$ group(s) independently of one another is(are) a Group 2-15 metal capable of complexing with the ligand to affect catalysis, wherein t=2, 3, or 4; and wherein the group(s) A independently of one another is(are) selected from the group consisting of neutral groups, bound and unbound anionic groups and combinations thereof, where s is the number of A groups associated to the metal and is 0, 1, or 2.

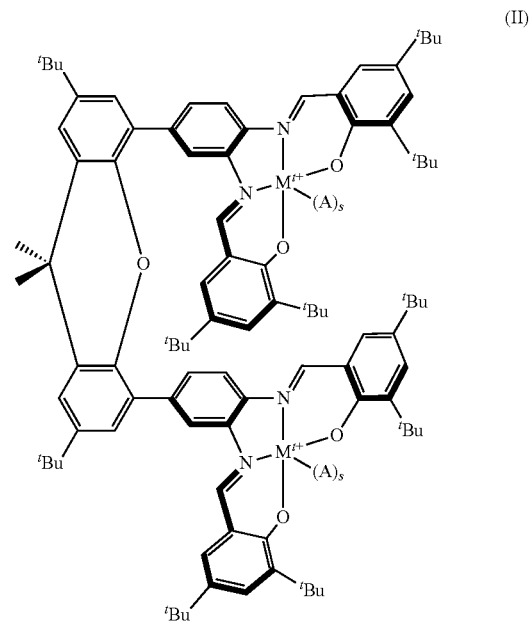

(II)

One embodiment is described by Formula III below, wherein the $M^{t+}$ group(s) independently of one another is(are) a Group 2-15 metal capable of complexing with the ligand to affect catalysis, wherein t=2, 3, or 4;

wherein the group(s) A independently of one another is(are) selected from the group consisting of neutral groups, bound or unbound anionic groups, and combinations thereof, where s is the number of A groups associated to the metal and is 0, 1, or 2; and wherein n=1-10 and mixtures thereof.

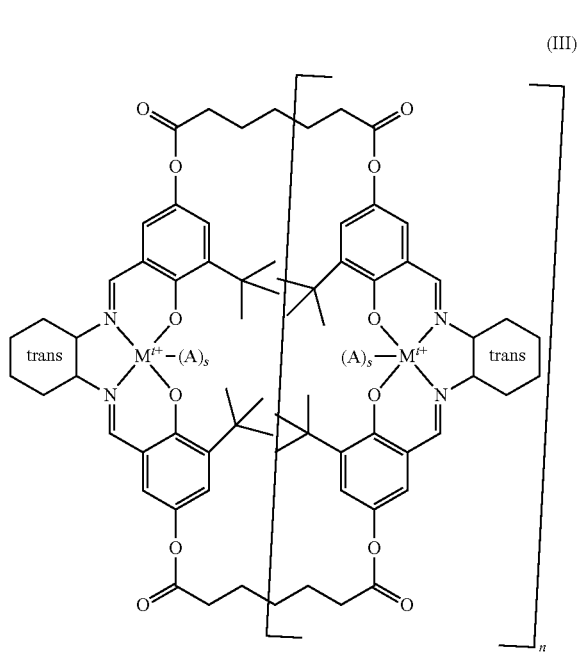

(III)

In an embodiment of the invention, the composition is present as an oligomer bound to a support. 'Bound' is defined as covalently bond, ionically bond, hydrogen bonded, metal complexed, encapsulated in a support and intercalated in a support, as described above. The support is selected from the group consisting of an organic polymer, ion-exchange resin, inorganic support, carbon, and mixtures thereof.

In an embodiment of the invention the racemic or non-racemic chiral monomeric composition is present wherein at least two monomeric metal ligand complexes are joined by a polyfunctional A to form a diasteriomeric mixture of molecules comprising more than one chiral monomeric ligand, where A is from a group containing a polycarboxylate (e.g. adipic acid), polysulfonate, and mixtures thereof.

In an embodiment of the invention, there is provided a process comprising, consisting of, or consisting essentially of contacting an alkylene oxide with 2-methoxy-1-propanol (PM1) in the presence of a catalyst comprising a tetradentate Schiff-base metal complex in a reaction zone under reaction conditions to produce a reaction product comprising alkoxylated PM1 with less than 10 alkylene oxide equivalents.

The catalyst is defined as a Schiff-base metal complex, wherein a monomer of the metal complex is defined by Formula (I). The catalyst can be any catalyst described in the previous embodiments, or any other monomeric catalyst defined by Formula (I).

The catalyst can be either homogenous or heterogeneous. The catalyst can be present as a monomer, oligomer, polymer or copolymer as described above. The catalyst can also be bound to a support, as described above.

In an embodiment, a cocatalyst can optionally be used. Generally, the cocatalyst is a Lewis acid. Examples of Lewis acids that can be used include, but are not limited to metal triflate, metal tosylate, tris-perfluoronated aryl borate, metal halides, and combinations thereof. An example of a metal triflate that can be used is aluminum triflate. When a cocatalyst is used, the mole ratio of the catalyst monomeric unit to the co-catalyst is generally in the range of from about 1:1 to about 20:1.

The alkylene oxide is generally selected from the group consisting of ethylene oxide, propylene oxide, butylene oxide, pentylene oxide, hexylene oxide, epihalohydrin and combinations thereof. In an embodiment, the alkylene oxide is propylene oxide.

The alkylene oxide and PM1 are generally present in a mole ratio of from about 0.01/1 to about 100/1. In an embodiment the reaction conditions includes a mole ratio of from 0.25/1 to about 10/1

The reaction conditions in the reaction zone generally include a temperature in the range of from about −10° C. to about 200° C. In an embodiment, the reaction conditions include a temperature in the range of from 0° C. to 60° C.

The reaction zone can be of the type comprising of a fixed bed, a fluidized bed, a continuous stirred tank reactor (CSTR), batch, semi-batch, continuous types or combinations thereof. Said reaction zone can be operated for example isothermally, adiabatically, or a combination thereof.

A reaction product is produced which comprises alkoxylated PM1 with less than 10 alkylene oxide equivalents. The reaction product generally comprises unreacted 2-methoxy-1-propanol (PM1), unreacted alkylene oxide, mono-alkoxylates of PM1, di-alkoxylates of PM1, and heavy molecular weight alkoxylates of PM1, which are alkoxylates with 3 to 10 alkylene oxide equivalents. The mono-alkoxylates of PM1 are typically present in the reaction product in an amount in the range of from about 0.1 weight percent to about 100 weight percent, based on the total weight of the reaction product. The di-alkoxylates of PM1 are typically present in the reaction product in an amount in the range of from about 0 weight percent to about 10 weight percent, based on the total weight of the reaction product.

In an embodiment of the invention, there is disclosed a process comprising, consisting of or consisting essentially of contacting an alkylene oxide with an alcohol in the presence of a catalyst comprising a tetradentate Schiff-base metal complex in a reaction zone under reaction conditions to produce a reaction product comprising a mixture of at least two components selected from the group consisting of a mono-alkoxylated alcohol, a di-alkoxylated alcohol, a tri-alkoxylated alcohol, and heavy molecular weight alkoxylated alcohols containing not more than 10 alkylene oxide equivalents.

In an embodiment, the alkoxylated alcohol products from above can optionally be contacted with additional alkylene oxide in the presence of the catalyst in a reaction zone under reaction conditions to produce a second reaction product with a mono-alkoxylated alcohol/di-alkoxylated alcohol product ratio less than in the first reaction product.

The catalyst is defined as an achiral or chiral tetradentate Schiff-base metal complex, wherein a monomer of said metal complex is defined by Formula (I). The catalyst can be any composition described in the above embodiments, or any other suitable composition defined by Formula (I) including monomeric forms.

The catalyst can be either homogenous or heterogeneous. The catalyst can be present as a monomer, an oligomer, a polymer or mixture thereof. The catalyst can also be bound to a support, as described above.

In an embodiment, a cocatalyst can also be used. The cocatalyst is a Lewis acid. Examples of Lewis acids that can be used include, but are not limited to metal triflate, metal tosylate, tris-perfluorinated aryl borate, metal halides, alkyl metals and combinations thereof. When a cocatalyst is used, the ratio of the catalyst monomer unit to the cocatalyst is generally in the range of from about 1:1 to about 20:1. In an embodiment, the Lewis acid is aluminum triflate.

Generally, alkylene oxide is selected from the group consisting of ethylene oxide, propylene oxide, butylene oxide, pentylene oxide, hexylene oxide, epihalohydrin and combinations thereof. In an embodiment, the alkylene oxide is propylene oxide.

Generally, the alcohol is selected from the group consisting of methanol, ethanol, propanol, butanol, pentanol, hexanol, 2-ethylhexanol, propylene glycol, ethylene glycol, glycerol, erythritol, pentaerythritol, trimethylolpropane, sorbitol, 2-methoxy-1-propanol, 1-methoxy-2-propanol, glycol ether, phenol and combinations thereof. In an embodiment, the alcohol is methanol.

In this embodiment, alkylene oxide and the alcohol are typically present in a ratio of from about 0.1/1 to about 10/1.

The reaction conditions in the reaction zone generally include a temperature in the range of from about −10° C. to about 200° C. In an embodiment, reaction conditions can include a temperature in the range of from 0° C. to 60° C.

The reaction zone can be of the type comprising of fixed bed, fluidized bed, continuous stirred tank reactor (CSTR), batch reactor, semi-batch reactor, continuous reactor or combination of thereof, said reaction zone can be operated for example isothermally, adiabatically, or a combination thereof.

The reaction zone of the optional secondary reaction step in this embodiment can be in either the same or different vessels as the reaction zone of the first reaction step.

A reaction product is produced which comprises alkoxylated alcohols with less than 10 alkylene oxide equivalents. The reaction product of the first and second reaction zones comprises at least two of monoalkoxylated alcohols (MA), dialkoxylated alcohols (DA), trialkoxylated alcohols (TA) and heavy molecular weight alkoxyated alcohols containing less than 10 alkylene oxide equivalents per molecule. The MA is present in said reaction product in an amount in the range of from about 10 weight percent to about 99.99 weight percent, based on the total weight of said reaction product. The DA is present in said reaction product in an amount in the range of from about 0.01 weight percent to about 80 weight percent, based on the total weight of said reaction product. The TP is present in said reaction product in an amount in the range of from about 0 weight percent to about 1 weight percent, based on the total weight of said reaction product.

The used catalyst can be isolated or concentrated in a process stream and recycled back to the reactor. Prior to recycling the catalyst may optionally be reactivated for example by treatment with acid, a source of oxygen, a metal capable of electron transfer, or a combination thereof.

EXAMPLES

The following examples are intended to be illustrative of the present invention and to teach one of ordinary skill in the art to make and use the invention. These examples are not intended to limit the invention in any way.

Preparation of Oligomeric-Salen Ligands

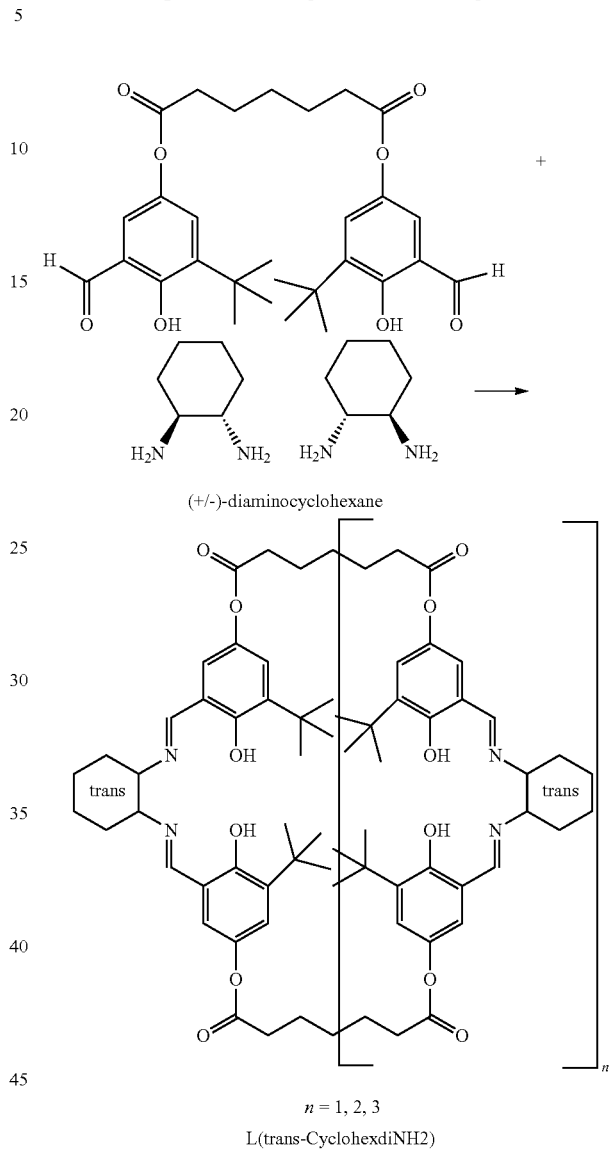

$n = 1, 2, 3$

L(trans-CyclohexdiNH2)

Preparation of Diasteriomeric Trans-Diaminocyclohexane Oligomeric Salen (L(trans-cyclohexdiNH2))

A round bottom flask (250 mL) was equipped with a Teflon coated stir bar and charged with Bis(3-t-butyl-5-formyl-4-hydroxyphenyl) heptanedioate (0.512 g, 0.999 mmol, synthesized as per procedure provided by White, D. E., Harvard University Thesis: "Development and mechanistic studies of a highly active and selective oligomeric (salen)Co(III) catalyst for asymmetric epoxide ring opening reactions" 2005, p. 172), trans-diaminocyclohexane (0.114 g, 0.999 mmol) and benzene (75 mL). The reaction was heated to 50° C. for 1.5 hours and checked for progression by HPLC at which time no remaining free dialdehyde was detected. The round bottom flask was fitted with a Dean-Stark trap and the reaction was refluxed for 8 hours overnight. An aliquot of the reaction mixture was diluted in fresh benzene and analyzed by HPLC showing two unresolved peaks at 21.715 and 21.751 minutes by evaporative light scattering detector. The reaction mixture was diluted with ethyl acetate (30 mL) and loaded into a separation funnel. The organic mixture was washed successively with d.i. water and brine. Upon phase separation, the organic layer was dried over MgSO$_4$, filtered and concentrated to dryness by rotary evaporation followed by in vacuo drying. By $^1$H NMR, it was determined that benzene was present in the product so the solids were dissolved in methylene chloride and concentrated by rotary evaporation twice and finally dried in vacuo, thus yielding yellow/brown crystalline solid 0.580 g (98%).

Preparation of L(Trans-cyclohexyldiNH2)-Co(III)-3NOBS Complex

Co(II) acetate tetrahydrate (0.036 g, 0.14 mmol) was made into a solution with 2 mL of methanol in an inert atmosphere box. This solution was added to a toluene (3 mL) solution of the L(trans-cyclohexyldiNH2) ligand (0.083 mmol) and allowed to stir under anaerobic conditions for 1.5 h. The mixture was concentrated under vacuum leaving a brick red solid residue. To this was added 0.083 mmol of 3-nitrobenzenesulfonic acid* 1H$_2$O and the mixture was taken up into 10 mL of methylene chloride and 2 mL of toluene. The mixture was removed from the glovebox and allowed to stir open to air overnight. After solvent removal the brownish/green solid, L(trans-cyclohexyldiNH2)-Co(III)-3NOBS, was used without further purification.

General Epoxide Ring Opening Procedure

L(trans-cyclohexyldiNH2)-Co(III)-3NOBS was weighed into a thick-walled vial fitted with a magnetic stir bar. To this was added a pre-mixed mixture of propylene oxide and methanol. The vial was capped and placed into an aluminum block on a stir plate and allowed to stir without added heat. The composition of the reaction mixture was examined by GC. Results are summarized in the following table:

| Catalyst | rac-PO (g) | MeOH (g) | Catalyst (g) | rxn time (h) | % PO conv | PM2/PM1 | PM/DPM + highers |
|---|---|---|---|---|---|---|---|
| L(trans-cyclohexyldiNH2)—Co(III)-3NOBS | 1.36 | 0.89 | 0.014 | 1.5 | 89% | 324 | 466 |

Synthesis of the Trans-Dimeric Ligand (5)

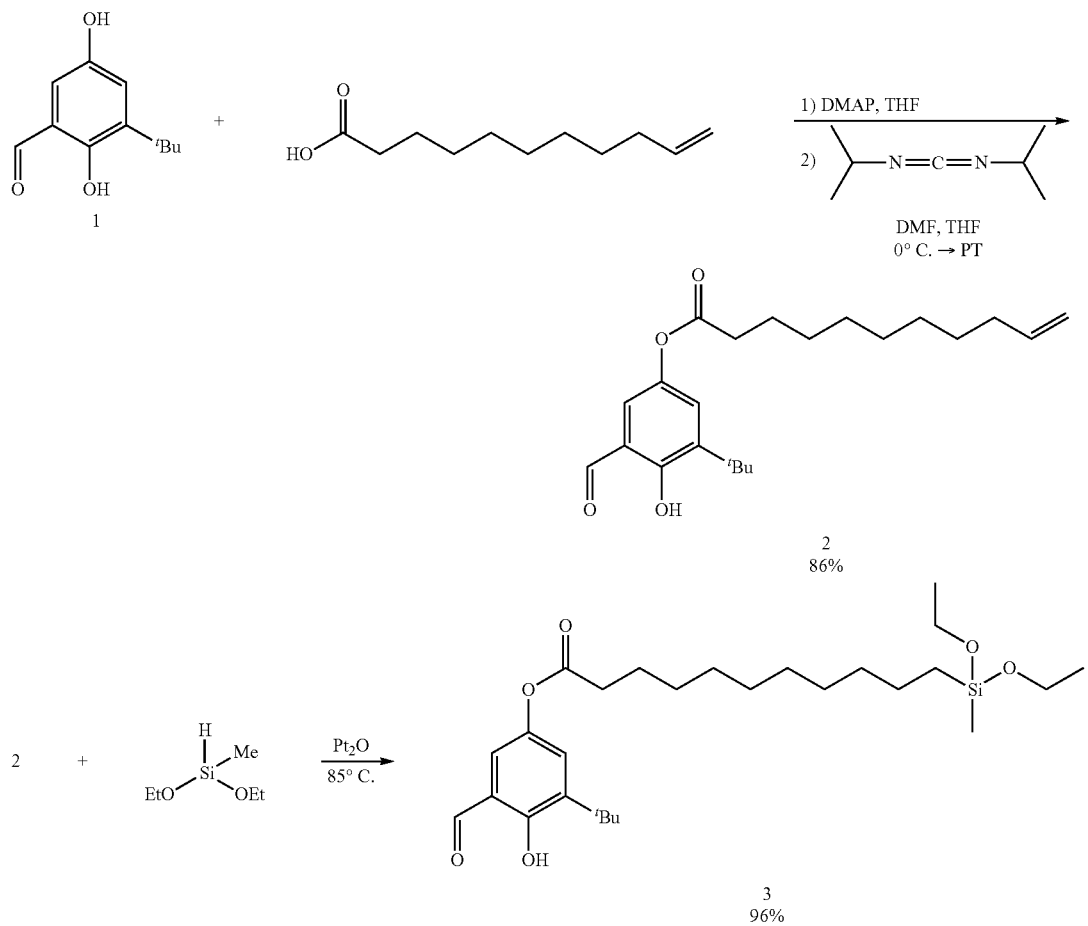

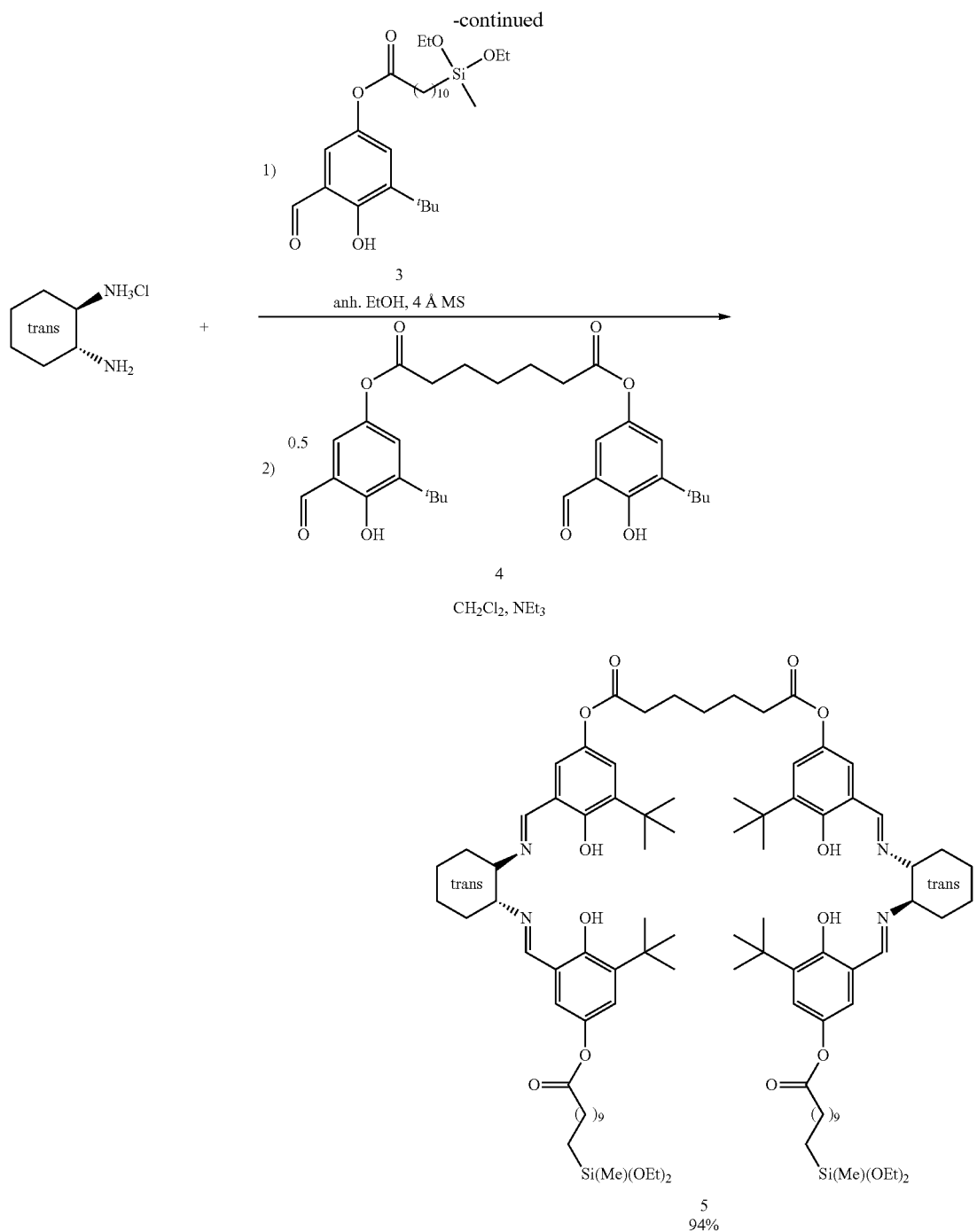

Synthesis of 10-undecenoic Acid, 3-tert-butyl-5-formyl-4-hydroxyphenylester (2)

A Schlenk flask equipped with a stir bar was charged with 3-tert-butyl-2,5-dihydroxybenzaldehyde (2.730 g, 14.06 mmol), 10-undecenoic acid (2.590 g, 14.06 mmol) and N,N-dimethylaminopyridine (0.172 g, 1.406 mmol). The flask was purged with N2 and THF (12 mL) and N,N-dimethylformamide (0.6 mL) were added. The mixture was cooled to 0° C. in an ice bath and N,N'-diisopropylcarbodiimide (1.86 mL, 14.76 mmol) was added. The mixture was stirred for 5 minutes at 0° C. then allowed to warm up to room temperature and stir overnight. The precipitated urea was filtered off and the mixture washed with 6 mL. THF was then removed under vacuum. The crude orange liquid was purified by flash chromatography using hexane:ethyl acetate (4:1) to give 4.354 g (86%) of a yellow-orange liquid. $^1$H NMR (RT, 500 MHz, $C_6D_6$): δ=12.09 (s, 1H), 9.08 (s, 1H), 7.30 (d, $J_{HH}$=5 Hz, 1H), 6.77 (d, $J_{HH}$=5 Hz, 1H), 5.79 (m, 1H), 5.02 (m, 2H), 2.33 (t, $J_{HH}$=13 Hz, 2H), 1.99 (m, 2H), 1.65 (m, 2H), 1.37 (s, 9H), 1.35-1.17 (m, 10H). $^{13}$C NMR (RT, 126 MHz, $C_6D_6$): δ=196.3, 171.6, 158.9, 143.1, 139.9, 139.1, 123.6, 120.5, 114.6, 35.25, 34.52, 34.30, 29.82, 29.72, 29.57, 29.55, 29.42, 29.27, 29.25, 25.37.

Synthesis of 3-tert-butyl-5-formyl-4-hydroxyphenyl-11-(diethoxy(methyl)silyl)-undecanoate (3)

In a 50 mL round-bottomed flask was weighed the olefin-tethered hydroxybenzaldehyde 2 (1.939 g, 5.379 mmol) and diethoxymethylsilane (0.939 g, 6.9924 mmol). Pt$_2$O (0.009 g, 0.040 mmol) was then added. The flask was equipped with a reflux condenser and the mixture was stirred at 85° C. for 20 hrs. After reaction, the mixture was taken up in anhydrous ethanol (20 mL) and filtered through activated carbon. Volatiles were then removed in vacuo to give 2.541 g (96%) of a yellow-orange oily liquid, 3, as a single regioisomer. Note: previous attempts at synthesizing 3 using stoichiometric amounts of diethoxymethylsilane led to small amounts of unreacted starting olefinic material. $^1$H NMR (RT, 500 MHz, C$_6$D$_6$): δ=12.12 (s, 1H), 9.06 (s, 1H), 7.31 (s, 1H), 6.76 (s, 1H), 3.71 (q, J$_{HH}$=7 Hz, 4H), 2.33 (t, J$_{HH}$=7.5 Hz, 2H), 1.67 (m, 2H), 1.53 (m, 2H), 1.37 (s, 9H), 1.35-1.20 (m, 10H), 1.17 (t, J$_{HH}$=7 Hz, 6H), 0.73 (m, 2H), 0.17 (s, 3H). $^{13}$C NMR (RT, 126 MHz, C$_6$D$_6$): δ=196.3, 171.6, 158.9, 143.1, 139.9, 123.6, 120.5, 58.24, 35.25, 34.53, 33.90, 30.10, 30.07, 29.95, 29.81, 29.62, 29.27, 25.40, 23.64, 18.92, 14.75, −4.28. $^{29}$Si NMR (RT, 99 MHz, C$_6$D$_6$): δ=−5.97 (s).

Synthesis of the Trans-Dimeric Schiff-Base Ligand (5)

In a two-necked 250 mL flask was placed trans-1,2-diaminocyclohexane monohydrochloride (0.500 g, 3.3190 mmol), the hydrosilylated tethered hydroxybenzaldehyde, 3, (1.642 g, 3.3190 mmol) and 4 Å molecular sieves (0.365 g). The flask was placed under a nitrogen atmosphere and anhydrous ethanol (25 mL) was syringed in to give a yellow mixture. The mixture was allowed to stir overnight. $^1$H NMR analysis of an aliquot showed the desired intermediate as the major product. A solution of the bis-hydroxybenzaldehyde, 4, (0.851 g, 1.660 mmol, synthesized as per procedure provided by White, D. E., Harvard University Thesis: "Development and mechanistic studies of a highly active and selective oligomeric (salen)Co(III) catalyst for asymmetric epoxide ring opening reactions" 2005, p. 172) in CH$_2$Cl$_2$ (10 mL) was syringed into the reaction flask, after which triethylamine (0.925 mL, 6.638 mmol) was slowly syringed in over 5 min. The reaction mixture was allowed to stir further for 18 hrs. After reaction, $^1$H and $^{13}$C NMR of an aliquot suggested the desired ligand was the major product of the reaction. The dark orange solution was passed through a thin pad of silica on top of a pad of Celite in a glass frit. The filtrate was roto-evaporated to give 2.578 g (94%) of a dark orange-brown oil, 5. No further purification was necessary. $^1$H NMR (RT, 500 MHz, C$_6$D$_6$): δ=14.08 (s, 4H), 7.77 (s, 2H), 7.75 (s, 2H), 7.21 (d, J$_{HH}$=2.5 Hz, 4H), 6.87 (d, J$_{HH}$=2.5 Hz, 4H), 3.71 (q, J$_{HH}$=7 Hz, 8H), 2.80 (m, 4H), 2.34 (t, J$_{HH}$=7 Hz, 4H), 2.28 (t, J$_{HH}$=7 Hz, 4H), 1.73-1.06 (m, 54H), 1.49 (s, 36H), 1.17 (t, J$_{HH}$=7 Hz, 12H), 0.71 (m, 4H), 0.17 (s, 6H). $^{13}$C NMR (RT, 126 MHz, C$_6$D$_6$): δ=171.8, 171.6, 165.4, 165.4, 158.4, 158.3, 142.7, 142.6, 138.9, 138.8, 123.4, 122.1, 122.0, 118.6, 71.88, 71.87, 71.83, 58.11, 35.15, 35.13, 34.49, 34.15, 33.73, 32.72, 29.94, 29.89, 29.77, 29.66, 29.47, 29.35, 28.71, 25.29, 24.78, 24.19, 23.44, 18.71, 14.53, −4.53.

Supporting Trans-Dimeric Ligand on Silica (Si-Trans-Dimer)

In a 250 mL flask was placed amorphous silica gel (0.846 g; 200 m$^2$/g, fully hydroxylated; previously activated in a 100° C. vacuum oven for 20 hrs). The trans-dimeric salen ligand, 5, (4.1 mL; as a 0.06143 M solution in CH$_2$Cl$_2$) was syringed on top of the silica. DMF was then added (2 mL). The slurry was stirred under N$_2$ at room temperature for 1 hr. Volatiles were then evaporated, after which the flask was placed in a 100° C. oil bath under full vacuum for overnight drying. The contents of the flask were rinsed with CH$_2$Cl$_2$ and filtered through a glass frit, with sequential washes of CH$_2$Cl$_2$, MeOH and CH$_2$Cl$_2$. The resulting yellow solid was dried in a vacuum oven at 55° C. for 24 hrs. Yield: 1.075 g, Si-trans-dimer. The yellow filtrate was concentrated in vacuo to yield 0.142 g of a yellow oil; ligand concentration based on weight difference is calculated as 158 μmol/g$_{solid}$, corresponding to 316 μmol/g for potential cobalt sites. Thermogravimetric analysis of a sample revealed a ligand concentration of 149 μmol/g$_{solid}$, corresponding to 298 μmol/g for potential cobalt sites.

Preparing Silica-Supported Trans-Dimeric Cobalt (III)-Salen Complex (Si-Trans-Dimer-Co(III)-3NOBS)

In a nitrogen-purged glovebox, a vial was charged with Si-trans-dimer (0.600 g, 0.089 mmol ligand) and a stir bar. In a separate vial, Co(OAc)$_2$.4H$_2$O (0.084 g, 0.3362 mmol) was dissolved in 3 mL of MeOH/toluene (1:1) to give a pink solution, which was then added to the supported ligand and allowed to stir for 60 min. The mixture immediately turned orange-red. The red mixture was filtered through a glass frit and washed with MeOH and CH$_2$Cl$_2$. The solid was then placed in a vial and 3-NO$_2$—C$_6$H$_4$SO$_3$H.xH$_2$O (where x is approximately 1) (0.041 g, 0.1849 mmol) was added as a suspension in CH$_2$Cl$_2$. The resulting mixture, which turned dark green, was allowed to stir overnight. After evaporation of the volatiles, the remaining green solid was rinsed and washed copiously with MeOH and CH$_2$Cl$_2$, before being dried in a vacuum oven to provide Si-trans-dimer-Co(III)-3NOBS.

Methanolysis of Propylene Oxide using Si-Trans-Dimer-Co(III)-3NOBS

In a thick-walled vial equipped with a stir bar was added the silica supported cobalt salen catalyst. Anhydrous methanol was then added to the vial via syringe, followed by addition of racemic propylene oxide in a 2:1 molar ratio, respectively. The vial was capped and the brown mixture was allowed to stir vigorously at room temperature for the indicated amount of time. Propylene oxide conversion and product distribution was obtained by GC. The results are summarized in the following table:

| Complex | Catalyst Loading (mol % WRT PO) | Rxn time (h) | PO Conversion (%) | PM2/PM1 |
|---|---|---|---|---|
| Si-trans-dimer-Co(III)-3NOBS | 0.05 | 2.8 | 96% | 252 |

Conditions: 2:1 MeOH/racPO mol ratio, room temperature

While this invention has been described in detail for the purpose of illustration, it should not be construed as limited thereby but intended to cover all changes and modifications within the spirit and scope thereof.

That which is claimed:

1. A composition comprising:
a racemic or non-racemic mixture of chiral Schiff base monomers, wherein a monomer is defined by the formula

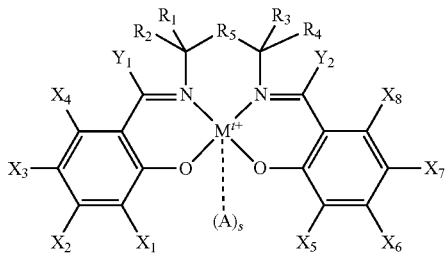

wherein $R_1$, $R_2$, $R_3$, $R_4$, $Y_1$, $Y_2$, $X_1$, $X_2$, $X_3$, $X_4$, $X_5$, $X_6$, $X_7$, and $X_8$ comprise, independently of one another, substituents selected from the group consisting of hydrogen, halogen, alkyl, alkenyl, alkynyl, hydrocarbyl, hydroxyl, alkoxyl, amino, nitro, amide, phosphoryl, phosphonate, phosphine, carbonyl, carboxyl, silyl, ether, thioether, sulfonyl, selenoether, ketone, aldehyde, and ester;
or wherein two or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ together form a ring selected from the group consisting of a carbocyclic ring and a heterocyclic ring, said ring having from 4 to 10 atoms in the ring;
wherein $R_5$ group is selected from the group comprising a carbon-carbon bond, a methylene group, an ethylene group, an amine, an oxygen atom, and a sulfur atom;
wherein one or more of $R_1$, $R_2$, $R_3$, $R_4$, $Y_1 Y_2$, $X_1$, $X_2$, $X_3$, $X_4$, $X_5$, $X_6$, $X_7$, and $X_8$ are capable of providing a complementary interaction to form a component selected from the group consisting of oligomer, polymer, and copolymer;
wherein $M^{t+}$ is a Group 2-15 metal capable of complexing with a ligand to affect catalysis, wherein t is an integer between 2 and 4;
wherein A is selected from the group consisting of neutral groups, bound anionic groups, unbound anionic groups and combinations thereof, wherein s is the number of A groups associated with the metal and is an integer between 0 and 2;
and wherein said composition is a diastereomeric mixture of components selected from the group consisting of oligomers, polymers, co-polymers, and combinations thereof.

2. A composition in accordance with claim 1 wherein said composition is present as an oligomer having from 1 to 20 repeat units.

3. A composition in accordance with claim 1 wherein said complementary interaction is selected from the group consisting of carbon-carbon coupling, condensation, etherification, amide formation, esterification, ring-opening polymerizations, olefin metathesis, olefin polymerization such as radical polymerization, cationic polymerization, anionic polymerization, group-transfer polymerization, heterogeneous Ziegler-Natta polymerization, and homogeneous Ziegler-Natta polymerization.

4. A composition in accordance with claim 1 wherein said composition is present as a polymer or a co-polymer having a molecular weight greater than 15,000.

5. A composition in accordance with claim 1 wherein said composition is bound to a support.

6. A composition in accordance with claim 1 wherein M is cobalt.

7. A composition in accordance with claim 1 wherein A is selected from the group consisting of a carboxylate, a sulfonate, a halide, an alkoxide, hexafluorophosphate, hexafluoroantimonate, tetrafluoroborate, and bis(trialkylsilyl)amide.

8. A composition in accordance with claim 1 where the composition is defined by the formula:

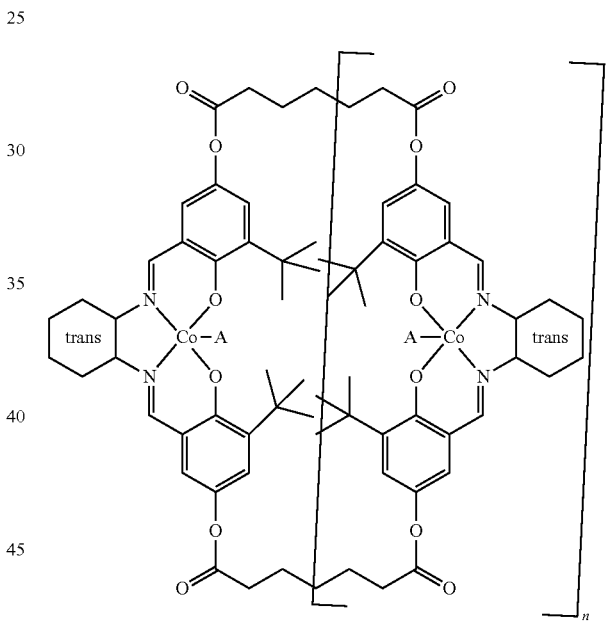

wherein A is 3-nitrobenzenesulfonate and n is an integer between 1 and 3.

* * * * *